United States Patent [19]

Kende et al.

[11] 4,021,457

[45] May 3, 1977

[54] INTERMEDIATES FOR POLYCYCLIC QUINONOID ANTIBIOTICS

[75] Inventors: Andrew S. Kende, Pittsford; John E. Mills, Rochester, both of N.Y.; Yuh-Geng Tsay, Taichung, China

[73] Assignee: Research Corporation, New York, N.Y.

[22] Filed: Apr. 5, 1976

[21] Appl. No.: 673,513

Related U.S. Application Data

[63] Continuation-in-part of Ser. No. 632,939, Nov. 18, 1975.

[52] U.S. Cl. ............................................. 260/383
[51] Int. Cl.² ....................................... C07C 49/70
[58] Field of Search .................................. 260/383

[56] References Cited

UNITED STATES PATENTS 2,922,691  1/1960  Grossman .................. 260/383 X

FOREIGN PATENTS OR APPLICATIONS 350,396    1/1961  Switzerland ................ 260/383
1,357,985  6/1974  United Kingdom ........... 260/383

*Primary Examiner*—Allen B. Curtis
*Attorney, Agent, or Firm*—Behr & Woodbridge

[57] ABSTRACT

There is provided a novel method of synthesizing certain tetracyclic quinones. In particular, there is provided a novel route to the synthesis of certain analogs of (+)-7-deoxydaunomycinone which includes the provision of novel tri- and tetracyclic quinone intermediates. The products of the synthetic route provided herein may be converted into compounds of known anti-neoplastic activity.

35 Claims, No Drawings

INTERMEDIATES FOR POLYCYCLIC QUINONOID ANTIBIOTICS

The invention described herein was made in the course of work under a grant or award from the Department of Health, Education and Welfare.

RELATED APPLICATIONS

This application is a continuation in part of our co-pending application Ser. No. 632,939 filed Nov. 18, 1975.

BACKGROUND OF THE INVENTION

The parent application of the present application, the disclosure of which is incorporated herein by reference, is directed to the synthesis of certain known antibiotics such as adriamycin and daunomycine. It has now been disclosed by Patelli, et. al. in Belgian Pat. No. 830090 assigned to Societa Farmaceutici Italia S.p.A. that certain analogs of daunomycine are useful in the therapy of neoplastic ailments. Included among these analogs are 4-demethoxydaunomycine, 1-methoxydaunomycine, 1,4- and 2,3-dimethyl-4-demethoxydaunomycine.

SUMMARY OF THE INVENTION

There is provided a novel process for the preparation of certain polycyclic quinones and polyquinones, in particular, there is provided a method of synthesizing analogs of daunomycinone.

The general reaction scheme is set forth herein below where $R_2O$ and $R_3O$ are ether groups, $R_7$ is hydrogen or alkyl, and $R_9$ is hydrogen, alkyl, or ether. In the preferred embodiments either $R_7$ or $R_9$ is hydrogen, though $R_7 = R_9 = H$ is permissible. In IX (a) $R_6$ is a lower alkanoyl and in IX (b) $R_6$ is hydrogen. $R_8$ is alkyl, substituted alkyl, phenyl or substituted phenyl.

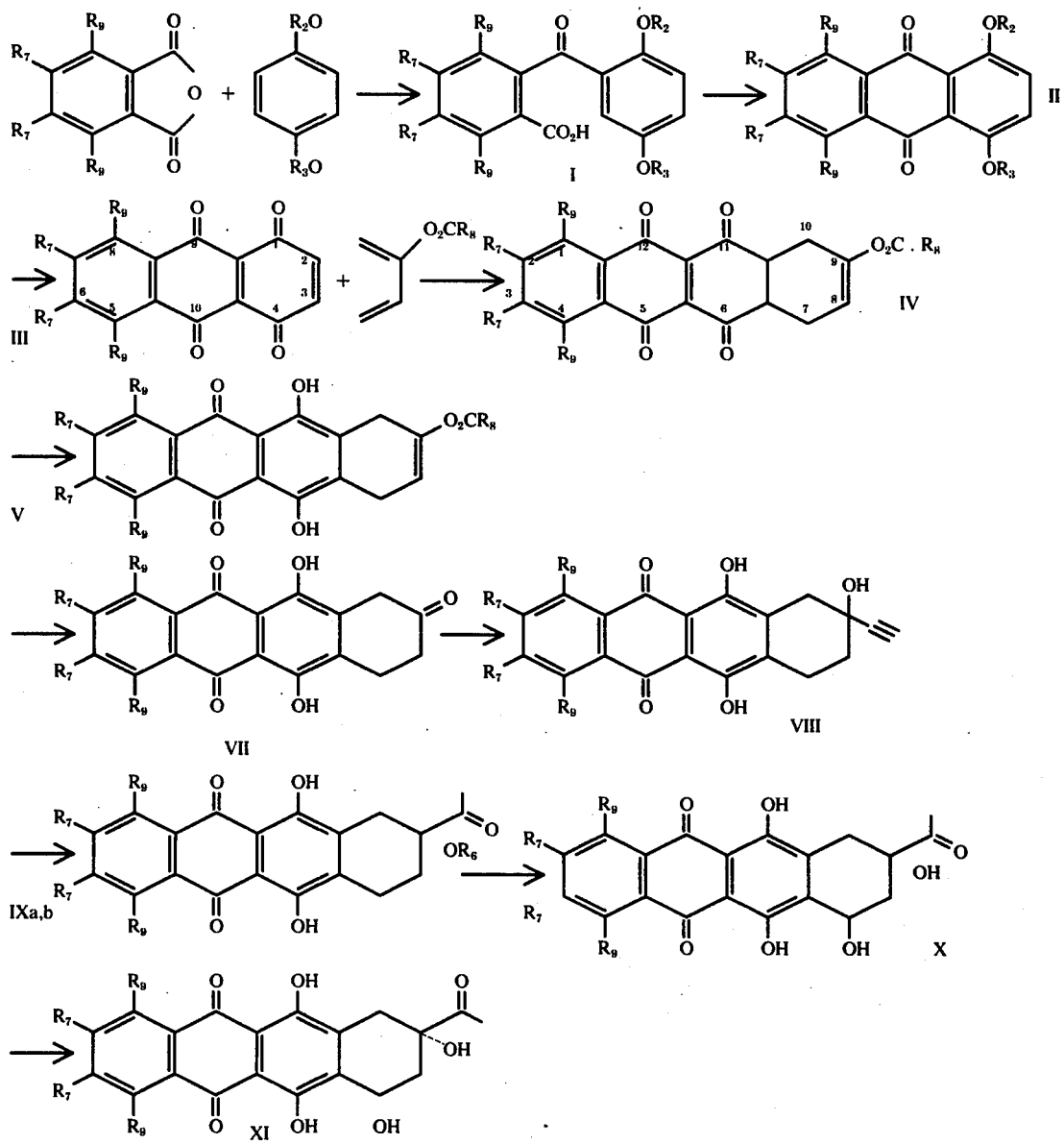

The actual starting materials for the reaction sequences set forth in the foregoing flow chart are the compounds of Formula (II). These compounds fall into two general categories. The first wherein the positions of the A ring — that is to say, the 5, 6, 7, and 8 positions of the quinzarinquinone moiety — ae unsubstituted or substituted, say at 5 and 8, or 6 and 7, by an alkyl group. The second category is that wherein the 5 and 8 positions are substituted by either moieties. In the first category the compounds of Formula II are readily prepared by a Friedel-Crafts reaction between the appropriate phthalic anhydride and the corresponding diether of hydroquinone. The resulting acid (I) is then ring closed by means of a cyclodehydrating agent, suitably concentrated sulfuric acid, anhydrous hydrogen fluoride or polyphosphoric acid, to yield the desired 1,4 diether (II).

The second category is prepared by the conversion of 1,8-diamino-4,5-dihydroxyanthraquinone into 1,4,5,8-tetraalkoxyanthraquinone suitably the tetramethoxyanthraquinone by methods well known in the art.

Compound (II) is then oxidized to yield the corresponding substituted quinizainquinone (III). Where compound (II) is a tetraether, it is preferred to use as oxidant silver (II) oxide in a suitable water-miscible organic solvent in the presence of mineral acid. Where compound (II) has $R_7 = R_9 = H$ or alkyl, oxidation may be carried out by heavy metal oxidants including ceric ammonium nitrate or by lead tetraacetate in acetic acid.

The quinizarinquinone compound (III) is then subjected to a Diels-Alder reaction with an ester of 2-hydroxy-1,3-butadiene to yield the 7,10-dihydro-5,6,11,12-naphthacenetetraone 9-ester (IV).

The compound (IV) is then reacted with a proton acceptor or proton donor in a suitable solvent to yield the corresponding 7,10-dihydro-6,9,11-trihydroxy-5,12-naphthacenedione 9-ester (compound V).

The 9-ester is then cleaved, suitably by mineral acid in a water-miscible organic solvent such as ethanol, aqueous acetic acid or tetrahydrofuran to yield 7,10-dihydro-6,11-dihydroxy-5,9,12(8H)-naphthacenetriones (compound VII). Mild base is also operative but not as efficient. The direct conversion of Diels-Alder adducts IV to compounds (VI) with strong acid in a water-miscible organic solvent is a feasible alternative to the two step sequence outlined above and proceeds in comparable yield.

Compound (VII) is then converted to the corresponding 9-ethynylcarbinol by reaction with an alkali metal acetylide or an ethynyl Grignard reagent to yield the 9-ethynyl-7,10-dihydro-6,9,11-trihydroxy-5,12(8H)-naphthacenedione (VIII). The ethynyl moiety of compound (VIII) is hydrated to yield the 9-acetyl-7,10-dihydro-6,9,11-trihydroxy-5,12(8H)-naphthacenedione (IX).

Compound (IX) may be converted into the corresponding 7-hydroxylated compound and thence to the desired end products by various methods. The introduction of the 7-hydroxyl may be accomplished by a novel variant of benzylic bromination followed by solvolysis. The subsequent glycosidation at the C-7 hydroxyl is achieved in the manner set forth by Acton, et. al. and Patelli, et. al. Belgian Pat. 830090.

Optical resolution of synthetic (+)-daunomycinone analogs is carried out by the conventional method of conversion to diastereomeric derivatives using a chiral resolving agent (Ct. Eliel, "Stereochemistry of Carbon Compounds", McGraw Hill, 1962, Chapter 4). In the preferred variants, the (+)-daunomycinone analog is monoesterified with 1-menthoxy acetyl chloride in pyridine, the diastereomeric C-7 esters separated by careful chromatography, and the ester derived from the (+)-daunomycinone analog cleaved with dilute base to give the (+)-daunomycinone analog.

The daunomycinone may be converted to the corresponding glycosides by methods well known and disclosed in the art.

DESCRIPTION OF THE PREFERRED EMBODIMENTS

Preparation of Starting Materials

The starting materials of the process of the present invention may be considered the compounds of formula (III) hereinabove. The 4-hydroxyquinizarinquinone of this general formula is a known compound and may be prepared either by the method of Dimroth and Hilcken (Ber., 54, 3050 (9121), or Kirk, et al, (U.S. Pat. No. 1,963.136). Where compound (III) is a 1,4-diether it is to be considered a novel compound and may be prepared by generally known methods from the appropriate ether of 3,6-dihydroxyphthalic anhydride. In this procedure, there may be employed any appropriate either, for example, the ether group may be alkyl, suitably lower alkyl, for example, methyl, ethyl, propyl, butyl, or pentyl. The ether may also be an aralkyl ether such as a phenyl-alkyl or substituted phenylalkyl ether, suitably where the alkyl is a lower alkyl, for example, wherein lower alkyl is as listed above and the substituents of which there may be between 1 and 5, and may be alkyl, suitably lower alkyl, such as those listed above, or alkoxy, suitably lower alkoxy such as the oxy derivatives of the lower alkyl moieties listed above, or halo, for example, fluoro, chloro, bromo or iodo. Furthermore, hereinabove and hereinbelow the prefix "lower alk" shall be considered as designating a saturated carbon skeleton bearing hydrogen atoms on said skeleton in all positions except where said skeleton is bonded to another group and containing 1–5 carbon atoms.

The phthalic anhydride is then subjected to a Friedel-Crafts reaction with hydroquinone, hydroquinone diether or hydroquinone diester. The ether groups $R_2O$ and $R_3O$ utilized may be the same as each other or different from each other and may be the same as or different from the ether moieties on the 3 and 6 positions of the phthalic anhydride with which it is to be reacted. Since however in a subsequent stage of this reaction, said ether groups are to be oxidatively removed to form a quinone moiety, it is preferred to utilize any readily available ether in this category of which p-dimethoxybenzene is preferred. In carrying out the Friedel-Crafts reaction, the 3-hydroxyphthalic anhydride or its derivatives is taken up in a dry reaction inert organic solvent to form a solution or suspension therein. The solvent utilized should of course be nonhydroxylic; solvents such as methylene chloride, nitrobenzene or carbon disulfide are considered suitable. To the mixture is added an excess, suitably about a 100% excess of anhydrous aluminum chloride. There is no specific temperature limitation upon the reaction, however, the reaction is rather slow at temperatures below 0° C, and proceeds too rapidly at elevated temperatures, thus it has been found advantageous to carry out the reaction at ambient temperatures, that is to say, at temperatures between about 10° and about 30° C, suitably about 20° C. To this solution is added the hydroquinone derivative in a similar solvent. There is utilized an excess of said hydroquinone derivative, suitably a 100% excess relative to the anhydride. The reaction mixture is stirred vigourously and after completion of the addition agitation is continued at ambient temperature for from about 12 to 36 hours.

The reaction is then quenched by pouring it onto a mixture of ice and concentrated hydrochloric acid. The slurry is agitated vigorously and then extracted with a water immiscible polar organic solvent, suitably a halogenated hydrocarbon solvent such as chloroform. Other organic solvents, for example, hydrocarbon solvents such as benzene, may be employed but are not preferred. During this extraction some of the desired ketoacid may precipitate and is collected by filtration.

The organic extract is washed with water, extracted with mild aqueous base, suitably saturated alkali metal carbonate or bicarbonate, such as sodium carbonate or bicarbonate, and said aqueous basic extract after washing with a fresh sample of the organic solvent used in the previous step, is acidified, suitably with a mineral acid, preferably with concentrated hydrochloric acid, cooled, suitably to between −5° and +5° C and the precipitate thereby formed is separated, preferably by filtration. There is thus obtained a product of general formula (I) in the foregoing flow chart which, except for the desired step of drying same to remove the moisture therefrom, is of sufficient purity for use in the next step of the reaction.

Compound (I) is then converted to the corresponding anthraquinone (II) by reaction with a cyclodehydrating agent. Any reagent which will thus dehydrate an O-benzoylbenzoic acid may be utilized. Among these reagents may be listed phosphorus pentoxide, polyphosphoric acid, anhydrous hydrogen fluoride and concentrated sulphuric acid; of these concentrated sulphuric acid is to be preferred. Compound (I) is added portionwise to a substantial excess of agitated concentrated sulphuric acid. After addition is complete the mixture is heated to moderately elevated temperatures suitably from about 70° to about 90° C, with constant agitation, for from about 15 to about 40, suitably from about 20 minutes. The now blue-colored mixture is cooled to ambient temperature and then the reaction is quenched by pouring onto crushed ice. The aqueous mixture is then extracted with a water immiscible organic solvent, preferably a polar organic solvent, suitably a halogenated hydrocarbon solvent, preferably chloroform, and the organic extract washed with dilute aqueous alkali, and then water, following which the extract is dried and the solvent removed to yield the desired product (II). It is preferred to further purify compound (II) and such purification may be achieved by recrystallization, suitably from a lower alkanol, such as ethanol or 2-butanol.

Compound (II) is then oxidized to Compound (III). Compound (II) is taken up in a reaction inert, water-miscible organic solvent. In view of the fact that the present step involves oxidation, said solvent should be relatively inert to oxidation. It has been found that ketones, suitably dialkyl ketones, preferably acetone, may be utilized. It is further preferred that the solvent be heated to a temperature at or near its boiling point.

To the warm solution is added a substantial excess of the oxidizing agent. It is preferred to utilize between 2 to 6 moles, suitably about 3 to about 5 moles of oxidizing agent per mole of compound (II). It has been found advisable to briefly sonicate the mixture to obtain uniform dispersal of the oxidant. Among the oxidizing agents which may be used as silver (II) oxide (argentic oxide) is especially preferred where $R_9$ is an ether group. The mixture is then heated and vigorously agitated. The reaction is then initiated by the addition of a small amount of acid, suitably mineral acid, preferably concentrated nitric acid. The reaction is rapid and should be considered complete in 10–30 minutes.

The acid utilized should be a strong acid, however, the quantity thereof is more critical than its nature. The amount of acid utilized should be just sufficient to dissolve all of the silver oxide. If an amount substantially greater than this is employed, the water present in the acid will interfere with the reaction and lower the yields obtained. The reaction mixture is then filtered, and the residue washed thoroughly with water and dried under reduced pressure to yield the appropriate diether compound (III) in sufficient purity to take part in the next stage of the reaction.

Where compound (II) has $R_2 = R_3 = H$ oxidation to (III) is preferably accomplished using lead tetraacetate in acetic acid.

The quinizarinquinone (Compound III) is taken up in an organic solvent, preferably in the presence of an organic acid and subjected to a Diels-Alder condensation with 2-hydroxy-1,3-butadiene 2-ester. Since the ester group at the 2 position of the butadiene will be removed in the next but one stage of the reaction sequence, the nature thereof is in no way critical. Any fairly readily hydrolyzable ester group may be employed. These include alkanoates, suitably lower alkanoates such as acetate, propionate, butyrate, valerate, and the like, aroyl esters for example benzoate and naphthoate, and their nuclearly substituted derivatives, aralkanoates, suitably aryl lower alkanoates, such as phenyl lower alkanoates, suitably benzylacetate, benzylpropionate, benzylbutyrate, and the like. Among these groups the acetate and the benzoate are to be preferred merely for reasons of ready accessibility and cost.

The reaction may be carried out in polar or nonpolar solvents, hydrocarbon solvents, suitably aromatic hydrocarbon solvents such as xylene or toluene may be employed, similarly halogenated hydrocarbons such as chloroform or methylene chloride may be used, equally mixtures of both of these groups of solvents may be employed. To improve the yield of the desired adduct it has been found advantageous to employ an organic acid as solvent or cosolvent. It has been found that lower alkanoic acids suitably acetic acid are to be preferred. It has been found suitable to prepare a solution of between 5 and 15% by weight of the reactants in a solvent mixture of the inert solvent and the acid. A mixture of 1 part of solvent to 2 parts (by volume) of the acid have been found suitable, although pure acetic acid is also satis factory. In order to maximize the yield of desired product, that is to say, a compound wherein the addition takes place as shown in compound IV, rather than at the 4a and 9a positions, the reaction should be carried out under the mildest conditions concommitant with reasonable reaction rates. Thus, it is preferred to run the reaction at ambient temperature, that is to say, between about 10° and about 40° C, suitably about 20° C for from about 2 to about 6 days under agitation, at about 20° C the time for completion of the reaction is about 4 days. The adduct (IV) formed in the reaction usually separates out as a precipitate and may be removed from the reaction mixture by filtration. The adduct may then be purified, suitably by washing with water and drying under reduced pressure.

The adduct (IV) is then enolized to the phenolic tautomer (V). The enolization is achieved by treatment of IV with a proton acceptor or proton donor in a suitable organic solvent. It has been found that salts of alkanoic, aroic or aralkanoic acid, such as acetates, butyrates, benzoates, naphthoates, phenyl acetates, phenyl propionates, and the like in the presence of the corresponding acid, suitably the same acid as that forming the anion of the salt, may be employed. The preferred conditions include, for example warming the compound in an alkanoic acid solvent containing either an alkali salt of that acid, or mineral acid, or p-toluene sulfonic acid. In the preferred variant of the reaction, the adduct is dissolved in glacial acetic acid at a temperature just below its boiling point, and the proton acceptor, preferably anhydrous sodium acetate, added thereto. There need only be utilized between 0.1 and 0.3 mg of the proton acceptor per mole of adduct. The enolization takes place very rapidly, but it is desirable to continue heating for 1 or 2 minutes after the addition. The reaction mixture is then cooled to ambient temperature, sufficient water added to precipitate the enolized adduct which is then separated suitably by filtration, washed, and dried under reduced pressure.

The two-step conversion of Diels-Alder adducts (IV) to the corresponding 9-ketones (VII) can be combined into one by warming compounds (IV) with a small amount of strong acid in a water-miscible organic solvent (e.g. lower alcohols), followed by work-up as described above for (VII). This alternative route proceeds in yields similar to the two-step sequence.

The enol ester (V) is then hydrolyzed to the corresponding 9-ketone (VII) While the hydrolysis itself is a step which is well known in the art, extreme care must be taken that in the course of this step the presence of oxidizing agents, in particular, air, are held to an absolute minimum in order to avoid unwanted aromatization of the saturated alicyclic ring. This aim is suitably achieved by degassing the reaction medium and carrying out the reaction in the presence of a substantially inert gas. For this purpose any of the inert gases or nitrogen may be utilized, nitrogen being preferred for reasons of cost. In the preferred procedure, the enol ester (V) is suspended in an alkanol, suitably a lower alkanol, for example, ethanol, the suspension degassed and the container flushed with nitrogen. There is added to the suspension, an excess of mineral acid, preferably 6N hydrochloric acid, since this acid does not have any oxidizing properties. Degassing and nitrogen flushing procedure is grain repeated, the mixture heated under reflux for from about 4 to about 8 hours, suitably for about 6 hours, cooled to ambient temperature, suitably about 20° C, diluted with water and the aqueous mixture extracted with a suitable immiscible organic solvent, preferably halogenated hydrocarbon solvent, such as chloroform. The chloroform extract is washed with water, dried, and the solvent removed to leave a residue which is then purified to yield the desired 9-ketone (VII) which is then purified.

Purification of the 9-ketone may be carried out by chromatography. Where small quantities are involved, chromatography on silica gel plates and elution with 5% hexane in chloroform or 3% methanol in methylene chloride has been found operative.

The ethynylation of compound (VII) may be carried out by reaction with an ethynyl Grignard reagent. In the preferred approach, acetylene is purified, suitably by passage thru, sequentially, alumina and concentrated sulphuric acid, and bubbled into a suitable ethereal solvent until said solvent is saturated with a sufficient quantity of acetylene, but bubbling is continued. Dioxan, tetrahydrofuran or diethylether may be employed, however, freshly distilled tetrahydrofuran under an inert atmosphere such as an nitrogen atmosphere is preferred. The acetylenic solution is then converted into the corresponding Grignard reagent in the usual manner, that is to say, a predetermined quantity of a suitable alkyl Grignard reagent, preferably a lower alkyl magnesium halide, most suitably ethyl magnesium halide, in an ethereal solution, is added in portions. When all of the said Grignard reagent has been added, the passage of acetylene is stopped and less than equimolar amount of a solution of compound (VII), preferably comprising about 0.01–0.2 moles relative to the Grignard reagent as prepared above, is added in a suitable ethereal solvent, preferably in dry tetrahydrofuran. The mixture is then agitated, suitably at ambient temperature, under an inert atmosphere, for from about 12 to about 18 hours. The reaction mixture is then quenched, preferably by the addition of cold saturated ammonium chloride solution, or aqueous oxalic acid, the organic (ethereal) phase set aside and retained, and the aqueous phase extracted with a suitable nonhydroxylic, water immiscible, organic solvent, preferably ethyl acetate. The ethyl acetate extract and the ether extract are then combined, dried, and evaporated to dryness to yield the ethynyl carbinol (VIII). This residue may be further purified.

The manner of purification is not critical and will depend upon the quantities available. It has been found found that chromatography on silica, utilizing as an eluent a mixture of an alkanol with an alkylene halide, suitably 3% methanol in methylene chloride may be employed.

The thus produced ethynyl carbinol (VIII) is then hydrated to form the desired 9-hydroxy-9-acetyl compound (IX).

In this procedure the ethynyl carbinol (VIII) is taken up in a reaction-inert polar organic solvent, suitably a halogenated hydrocarbon such as chloroform, methylene chloride, or the like. There is also prepared a fresh solution of mercuric ion, preferably in the presence of a mineral acid. The source of the mercuric ion is not critical, salts of mineral acids such as mercuric sulphate or salts or organic acids, such as mercuric acetate or the yellow mercuric oxide itself, may be employed. It is generally preferred to utilize yellow mercuric oxide in a small amount of water containing about 15% per volume of concentrated sulphuric acid. The acidic solution is warmed to between 60 to 80° C, the solution of the carbinol added thereto, and the mixture heated, suitably under reflux, for from about 2 to about 6, suitably from about 4 hours, cooled to ambient temperature, quenched in water, and extracted with a suitable solvent, for example, a water immiscible organic solvent such as chloroform or the like. The organic extracts are washed, treated with a mild base, suitably saturated sodium bicarbonate, to remove residual traces of acid, dried and the solvent removed.

The residual material, compound (IX), may be then further purified, suitably by chromatography, preferably on silica gel, to yield the racemic mixture of the desired product.

In an alternative procedure, compounds (VIII) may be converted to the 9-acetates or trifluoroacetates of compounds (IX) by stirring with mercuric acetate or trifluoroacetate respectively in an inert polar organic solvent, preferably ethyl acetate. Under these reaction conditions, certain compounds of type (VIII) lead directly or in part to the free 9-hydroxy compounds (IX), isolated as noted above. Subsequent treatment of the 9-esters by dilute aqueous base yields the free 9-hydroxy compounds (IX), isolated and purified as described above.

As stated above, the compounds of general formula (IX) may be converted to the 7-hydroxylated compounds by a sequence proceeding through benzylic bromination.

Although similar chemistry utilizing N-bromosuccinimide on related but different substrates has been reported by Wong, et. al, (Canad. J. Chem., 51, 446, (1973), that reagent is generally unsatisfactory when applied to intermediates of our invention.

Compound (IX) is treated with a free radical source of bromine under conditions which substantially reduce the accumulation of hydrobromic acid.

Suitably, compound (IX) is taken up in an inert, non-polar organic solvent. Bromine, in a similar solvent, is added in the presence of a free radical source, suitably a source of ultra violet light. The concentration of hydrobromic acid is reduced to preclude conditions of ionic bromination, a stream of inert gas, suitably a stream of nitrogen is passed continuously thru the reaction system. Other means of elimination of the acid may also be employed. Specifically, dry nitrogen is bubbled through a dilute solution of compound (IX b) in carbon tetrachloride. The solution is irradiated with a sunlamp while a dilute solution of bromine in carbon tetrachloride is added (in large excess, say from 2–6 fold excess) over several, say, 1–4 hours, under steady nitrogen bubbling and stirring. The brominated material is not isolated as such but is merely concentrated. The brominated material is then hydrolyzed to replace the bromine at the 7-position with a hydroxyl. The hydrolysis may be one stage or two stage.

In the single stage method, there is used water, mild base, such as aqueous alkali, an alkaline earth metal carbonate, such as sodium carbonate or calcium carbonate. Hydrolysis may be achieved in substantially non-aqueous media by passing a solution of the brominated material in an organic solvent over alumina or silica gel. While the reaction is carried out in a substantially dry environment — since otherwise the alumina on the silica gel would clog, it is advisable for either the solvent or, the alumina or the silica gel to contain some water, up to 10% by weight is suitable. Preferably, the residue taken up in chloroform, and the chloroform solution run through silica, either in the form of silica gel column or a silica gel plate. Elution with a suitable solvent, for example 3% methanol in methylene chloride, yields a mixture of the daunomycinone and 7-epidaunomycinone analogs, and recovered starting materials in an approximate ratio of 2:3:1.5

In the two-stage hydrolysis, the brominated material is treated with a suitable derivative of an alkanoic acid, an ester or the silver salt of an alkaline acid may be employed, suitably the silver salt is used. Most suitably, silver trifluoroacetate is employed. The thus produced 7-trifluoroacetate is readily removed, suitably with mild base to yield the desired 7-hydroxy derivative.

The epianalogs may be readily converted to the desired daunomycinone analog by acid epimerization. In this procedure the epianalog is taken up in trifluoroacetic acid, allowed to stand at ambient temperature from about 1 to about 3 hours, quenched in water, extracted with a water immiscible polar non-hydroxylic solvent, preferably halogenated hydrocarbon solvent, such as chloroform, the solution washed with water, dried and chromatographed as set forth above, to yield the desired daunomycinone analog in approximately 75% yield.

EXAMPLE I 2-(2', 5'-Dimethoxybenzoyl) benzoic acid (I)

Phthalic anhydride (17.8 g, 0.1 mole) is suspended in 100 ml. dry methylene chloride (previously distilled over anhydrous potassium carbonate). To the suspension is added anhydrous aluminum chloride (30.5 g, 0.23 mole) in one portion. The suspension quickly became bright yellow and is stirred at room temperature for 2 hours. A solution of p-dimethoxybenzene (27.6 g, 0.2 mole) in methylene chloride (100 ml) is added slowly to the vigorously stirred solution. The reaction mixture is stirred overnight at 25° and poured onto ice (300 g) and concentrated hydrochloric acid (50 ml). The slurry was stirred for 30 minutes and extracted with chloroform (4 × 150 ml). A white precipitate suspended in the aqueous layer is collected by filtration. The organic extract was washed once with water (200 ml) and washed with saturated sodium bicarbonate (4 × 150 ml). The aqueous bicarbonate extract is washed once with chloroform (150 ml) and acidified with concentrated hydrochloric acid, the mixture cooled on an ice bath and filtered. The residue is washed well with water and dried under reduced pressure and combined with the white precipitate to yield 2-(2', 5'-dimethoxybenzoyl) benzoic acid (I) as a pale yellow solid.

In accordance with the above procedure but starting with 3,6-dimethyl phthalic anhydride or 4,5-dimethyl phthalic anhydride there is obtained 2-(2', 5'-dimethoxy benzoyl)-3,6-dimethyl benzoic acid and 2-(2', 5'-dimethoxy benzoyl)-4,5-benzoic acid.

In accordance with the foregoing procedures, but where in place of p-dimethoxybenzene, there is used hydroquinone, there is obtained the corresponding 2-(2', 5'-dihydroxybenzoyl)-benzoic acid.

EXAMPLE II 1,4-Dimethoxyanthraquinone (II)

2-(2', 5'-Dimethoxybenzoyl)-benzoic acid (I) (3 g, 0.01 mole) is added in portions to stirred concentrated sulfuric acid (20 ml). After addition the mixture is heated on steam bath with constant stirring for 20 minutes, cooled to room temperature and poured onto crushed ice (400 g) and extracted with chloroform (3 × 100 ml). The organic extract is washed with 2% aqueous sodium hydroxide solution (10 × 100 ml) and water (100 ml), then dried over anhydrous sodium sulfate and the solvent stripped off under reduced pressure to yield 1,4-dimethoxyanthraquinone (II), as a brownish yellow solid.

In accordance with the above procedure by starting with other benzoic acids prepared in accordance with Example I there is obtained 5,8-dimethyl-1,4-dimethoxyanthraquinone and 6,7-dimethyl-1,4-dimethoxyanthraquinone respectively.

EXAMPLE III

Quinzarinquinone III 1,4-Dimethoxyanthraquinone (II) (0.596 g, 2 mmole) is dissolved in hot aceton (60 ml) and argentic oxide (1g, 8mmole) was added to this warm solution. Brief sonication forms a uniform dispersal of oxident. The mixture is heated up to boiling on steam bath again and the mixture stirred vigorously with magnetic stirrer. The oxidation is then initiated by the addition of 6N aqueous nitric acid (2 ml). After addition, the mixture is stirred while cooling for an extra 20 minutes and filtered. The residue is washed thoroughly with water and dried under reduced pressure to give quinizarinquinone (III) as a brown solid.

In accordance with the above procedure, but where in place of 1,4-dimethoxyanthraquinone there is utilized 1,4,5,8-tetramethoxyanthraquinone, there is obtained the corresponding 1,4-dimethoxy-5,8,9,10-anthradiquinone as a purple solid, m.p. 277–278; NMR: $\delta$ 3.96 (s, 6H), 6.89 (s, 2H), 7.37 (s, 2H); IR: 5.93, 6.10, 6.41 microns.

In accordance with the above procedure but where in place of 1,4-dihydroxyanthraquinone there is utilized 1,4-dimethoxy-5,8-or 6,7-dimethylanthraquinone, there is obtained the corresponding 1,4-dimethyl-5,8,9,10-anthradiquinone or 2,3-dimethyl-5,8,9,10-anthradiquinone.

EXAMPLE IV

1,4,9,10-Anthradiquinone

A mixture of 1,4-dihydroxyanthraquinone (10.0 g), lead tetraacetate (20 g) and acetic acid (25 ml) was ground together in mortar and pestle for 10 minutes at 25°. The reaction mixture was filtered and the solid washed with acetic acid, water, and ether. The red solid was taken up in a large volume of aceton (700 ml), the solution filtered through Celite, dried over sodium sulfate and evaporated under reduced pressure to give 1,4,9,10 anthradiquinone (8.2 g, 81% yield) as a brown solid. m.p. 213°–215° C (benzene/pet. ether) lit m.p. 211°–213° NMR (CDCl$_3$) $\delta$8.2–7.8 (m, 4H aryl), 6.88 (s, 2H); IR 5.96, 610 (sh), 6.15 (sh), 6.3$\mu$.

In accordance with the above procedure but where in place of 1,4-dihydroxyanthraquinone there is utilized 1,4-dihydroxy-5,8-or 6,7-dimethylanthraquinone there is obtained the corresponding 1,4-dimethyl-5,8,9,10-anthradiquinone or 2,3-dimethyl-5,8,9,10-anthradiquinone.

EXAMPLE V

6a,7,10,10a-Tetrahydro-9-hydroxy-5,6,11,12-naphthacenetetraone 9-acetate (IV)

1,4,9,10-anthradiquinone (III) (4.8g) and 2-acetoxy-1,3-butadiene (3.68 g) were stirred in acetic acid (24 ml) at room temperature for 40 hours. A tan colored solid precipitate separated and was washed well with acetic acid and ether. After drying under reduced pressure at ambient temperature 6a,7,10,10a-tetrahydro-9-dihydroxy-5,6,11,12-naphthacenetetraone 9-acetate (IV) was obtained (5.65 g, 81% yield). m.p. 180°–182° C (benzene/pet. ether) PFT (CDCl$_3$) $\delta$8.1–7.3 (m, 4H aryl), 5.44 (m, 1H olefinic), 3.61 (m,2H bridge protons), 2.52 (m, 4H allylic), 2.13 (s, 3H OCCH$_3$); IR 5.74 (sh), 5.88, 604 u; UV 350 nm (CHCl$_3$); MS 352 (M + 2), 350 (M), 308 (M-CH$_3$CO).

In accordance with the above procedures, but where in place of 2-acetoxy-1,3-butadiene there is utilized 2-propionoxy- or 2-benzoyloxy-1,3-butadiene, there is obtained the corresponding 9-propionate, or 9-benzoate respectively.

Similarly, but where in place of 1,4,9,10-anthradiquinone, there is utilized 1,4- or 2,3-dimethyl-5,8,9,10 anthradiquinone, there is obtained 1,4-dimethyl or 2,3-dimethyl-6a,7,10,10a-tetrahydro-9-hydroxy-5,6,11,12-naphthacenetetraone 9-acetate.

EXAMPLE VI

7,10-Dihydro-1,4-dimethoxy-6,9,11-trihydroxy-5,12 naphthacenedione 9-acetate-(IV)

1,4-Dimethoxy-5,8,9,10-anthradiquinone (230 mg) was placed in a flask with cupric acetate (2 mg) and 2-acetoxybutadiene (230 mg). Glacial acetic acid (2 ml) was added, and the reaction mixture was heated at 110° with stirring for 3 hours. The mixture was allowed to cool to room temperature, then treated with ~8 ml of ether. The precipitate was filtered and dried under vacuum to yield 167 mg (53%) of the enolized Diels-Alder product as a red solid. m.p. 232°–235°. NMR: $\delta$2.18 (s, 3H), 3.51 (broad s, 4H), 4.01 (s, 6H), 7.37 (s, 2H), 13.70 (s, 2H); IR: (CHCl$_3$) 5.70, 6.23; MS: 410, 408, 368, 353, 351, 340, 338, 325; Analysis: Calculated: C 64.38, H 4.42 Found: C 64.40, H 4.28%.

The mother liquor from this reaction can be poured into water, extracted with chloroform. The chloroform extracts washed with saturated aqueous sodium bicarbonate and water, dried over sodium sulfate, concentrated, and eluted down a florisil column — start with CH$_2$Cl$_2$ gradually increasing polarity to 3% MeOH/CH$_2$Cl$_2$ v/v) — to yield mainly 1,4-dihydroxy-5,8-dimethoxyanthraquinone, and some additional Diels-Alder product.

1,4-Dihydroxy-5,8-dimethoxyanthraquinone is a new compound: m.p. 297°–300°. NMR: $\delta$4.02 (s, 6H), 7.24 (s, 2H), 7.38 (s, 2H), 13.06 (s, 2H); MS: m/e 300, 285 (—CH$_3$), 282 (—H$_2$O), 272 (—CO), 270 (—2CH$_3$), 267 (—CH$_3$—H$_2$O), 264 (—2H$_2$O); Analysis: Calculated: C 64.00, H 4.03, Found: C 64.03, H 4.20%.

EXAMPLE VII

7,10-Dihydro-6,9,11-trihydroxy-5,12-naphthacene dione 9-acetate (V)

6a,7,10,10a-tetrahydro-1,9-dihydroxy-5,6,11,12-naphthacenetraone 9-acetate (IV) (50 mg) was dissolved in 1 ml. glacial acetic acid at 130°–135°. To this solution was added anhydrous sodium acetate (24 mg, 2.0 equiv.). After addition, the mixture was heated for an extra 2 minutes during which time a red precipitate formed, and cooled to 90° C, and diluted with water (2 ml) and cooled to room temperature. More water (5 ml) was added, and the precipitate filtered. The precipitate was washed well with water and ether and dried under reduced pressure to give 7,10-dihydro-6,9,11-trihydroxy-5,12-naphthacenedione-9-acetate (V) as a red solid (41 mg, 82% yield). m.p. 208°–210°. PFT (CDCl$_3$) $\delta$13.33 (s 1H OH), 13.30 (s 1H OH), 8.29 (m 2H aryl), 7.79 (m 2H aryl), 5.61 (bs 1H olefinic), 2.22 (s 3H OCCH$_3$); IR 5.75, 6.20, 6.38$\mu$; UV 517, 483, 460 and 282 nm (CHCl$_3$); MS 350 (M$^+$), 308 M-CH$_3$CO).

In accordance with the above procedure, but starting with 1,4-dimethyl and 2,3-dimethyl-6a,7,10,10a-tetrahydro-9-hydroxy-5,6,11,12-naphthacenetetraone 9-acetates, there are obtained the corresponding 7,10- dihydro-6,9,11-trihydroxy-1,4-dimethyl, and 2,3-dimethyl-5,12-naphthacenedione 9-acetates.

EXAMPLE VIII

7,10-Dihydro-6,11-dihydroxy-5,9,12(8H)-naphthacenetrione (VII)

The red enolacetate (7,10-dihydro-6,9,11-trihydroxy-5,12-naphthacenedione 9-acetate was suspended in ethanol (60 ml). The suspension was degassed and flushed with nitrogen. 6N hydrochloric acid (25 ml) was added to the mixture which was again degassed and flushed with nitrogen. The mixture was stirred at 80°–85°for 1.5 hours under nitrogen, cooled to room temperature and the red precipitate filtered was washed well with water and ether and dried under reduced pressure to give a dark red residue (850 mg, 96%) of 7,10-dihydro-6,11-dihydroxy-5,9,12(8H)-naphthacenetrione (VI). m.p. 320 (decomp.); PFT $\delta$13.47 (s 1H OH), 13.37 (s 1H OH), 8.37 (m 2H aryl), 7.56 (m 2H aryl), 3.67 (s 2H benzylic), 3.28 (t 2H benzylic), 2.66 (t 2H allylic); UV 517, 484, 458, 287, 257, 252 nm (CHCl$_3$); IR 5.88, 6.20, 6.37$\mu$; MS 310 (M$^+$), 282 (M-CO).

In accordance with the above procedure but starting with 7,10-dihydro-1,4-dimethoxy-6,9,11-trihydroxy-5,12-naphthacenedione 9-acetate there is obtained 7,10-dihydro-1,4-dimethoxy-6,11-dihydroxy-5,9,12 (8H)-naphthacenetrione. m.p. 173°–174°(sealed tube). NMR: $\delta$13.71 (s, 1H), 13.59 (s, 1H), 7.43 (s, 2H), 4.04 (s, 6H), 3.58 (s, 2H), 3.20 (t, 2H, J = 7 Hz), 2.64 (t, 2H, J = Hz); MS: 368, 353, 350, 340, 325, 322, 311.

In accordance with the above procedures but starting with 7,10-dihydro-1,4-dimethyl or 2,3-dimethyl-6,9,11-trihydroxy-5,12-naphthacenedione 9-acetate there is obtained the corresponding 7,10-dihydro-1,4-dimethyl or 2,3-dimethyl-6,11-dihydroxy-5,9,12 (8H)-naphthacenetrione.

In accordance with the above procedures, but where in place of the 9-acetate there is used the 9-benzoate, the same product is obtained.

EXAMPLE IX

9-Ethynyl-7,10-dihydro-6,9,11-trihydroxy-5,12(8H)-naphthacedione (VIII)

Acetylene, purified by passing it first through a column of alumina, then through concentrated sulfuric acid, was bubbled rapidly through freshly distilled tetrahydrofuran (100 ml) under nitrogen for 30 minutes. Ethylmagnesium bromide (3 ml, 3.15 M in ether, 12.6 mmole) was added in portions. When the frothing subsides, portionwise addition of the ethylmagnesium bromide solution was continued until the total solution had been added. The passage of acetylene was stopped and 7,10-dihydro-6,11-dihydroxy-5,9,12(8H)-naphthacenedione (VII) (250 mg, 0.12 mmole) in dry tetrahydrofuran (240 ml) was added dropwise. An immediate blue color was noted. After addition was completed, the mixture was stirred at room temperature under dry nitrogen overnight. To the dark blue solution was added 5% aqueous oxalic acid solution until the blue color disappeared and the brown reaction mixture extracted with chloroform. The chloroform extracts were washed well with water, dried over anhydrous sodium sulfate and the solvent removed to give a dark residue. The residue was chromatographed on Florisil (100–200 mesh) elution with methylene chloride, then with 2% methanol/methylene chloride yielded 9-ethynyl-7,10-dihydro-6,9,11-trihydroxy-5,12(8H)-naphthacenedione (VIII) (200 mg, 91%) as a red orange solid. m.p. 230° C with decomposition; IR 6.15, 6.30$\mu$; MS 334 (M$^+$) 317 (M-OH); NMR (CDCl$_3$) 13.40 (s 2H OH's), 8.3 (m 1H aryl), 7.7 (m 1H aryl), 3.1 (m 4H benzylic), 2.5 (s 1H ethynyl), 2.16 (m 2H allylic); UV (CHCl$_3$) 289, 460, 485, 518 nm; PFT (CDCl$_3$) $\delta$13.46 (s 2H OH), 8.34 (m 2H aryl), 7.81 (m 2H aryl), 2.06 (t 2H benzylic), 2.50 (s 1H ethynyl), 2.15 (t 2H allylic).

In accordance with the above procedure but starting with 7,10-dihydro-1,4-dimethoxy-6,11-dihydroxy-5,9,12(8H)-naphthacenetrione there is obtained 9-ethynyl-7,10-dihydro-1,4-dimethoxy-6,9,11-trihydroxy-5,12(8H)-naphthacenedione. NMR: $\delta$= 13.72 (s, 2H), 7.39 (s, 2H), 4.03 (s, 6H), 3.04 (m, 4H), 2.48 (s, 1H), 2.12 (m, 2H), 3.48 (s, 1H, OH); MS: 394, 376.

Similarly in accordance with the above procedure but starting with 7,10-dihydro-1,4-dimethyl or 2,3-dimethyl-6,11-dihydroxy-5,9,12(8H)-naphthacenetrione, there is obtained 9-ethynyl-7,10-dihydro-1,4-dimethyl or 2,3-dimethyl-6,9,11-trihydroxy-5,12(8H)-naphthacenedione.

EXAMPLE X

9-Acetyl-7,10-dihydro-6,9,11-trihydroxy-5,12(8H)-naphthacenedione 9-acetate (IX) (a)

9-ethynyl-7,10-dihydro-6,9,11-trihydroxy-5,12(8H)-naphthacenedione (15 mg) and mercuric acetate (29 mg) were suspended in ethyl acetate (10 ml) and the mixture stirred at room temperature for six hours. Hydrogen sulfide gas was bubbled through until no more black precipitate was formed. More ethyl acetate (5 ml) was added and the reaction mixture was filtered through celite and the filtrate evaporated to dryness. The residue was chromatographed on silica prep plates, and eluted with 3% methanol/methylene chloride to 9-acetyl-7,10-dihydro-6,9, 11-trihydroxy-5,12(8H)-naphthacenedione 9-acetate (11mg, 62% yield). m.p. 234°–237° C (CH$_3$CO$_2$H); z IR 5.80, 6.19, 6.34$\mu$; UV 518, 484, 460, 290 nm (CHCl$_3$); PFT (CDCl$_3$) $\delta$13.44 (s 2H OH), 8.34 (m 2H aryl) 7.82 (m 2H aryl) 3.21 (s 4H benzylic), 2.25 (s 3H OCCH$_3$), 2.08 (s 3H OOCH$_3$); MS 394 (M$^+$), 334 (M-CH$_3$CO$_2$H).

In accordance with the above procedure but starting with 9-ethynyl-7,10-dihydro-1,4-dimethoxy-6,9,11-trihydroxy-5,12(8H)-naphthacenedione there is obtained 9-acetyl-7,10-dihydro-1,4-dimethoxy-6,9,11-trihydroxy-5,12(8H)-naphthacenedione 9-acetate. NMR: (partial) : $\delta$2.08 (s, 3H), 2.23 (s, 3H), 4.05 (s, 6H), 7.44 (s, 2H), 13.76 (s, 2H); MS: 454, 394, 379, 376, 369, 351, 333.

In accordance with the above procedure but starting with 9-ethynyl-7,10-dihydro-1,4-dimethyl or 2,3-dimethyl-6,9,11-trihydroxy-5,12(8H)-naphthacenedione there is obtained 9-acetyl-7,10-dihydro-1,4-dimethyl or 2,3-dimethyl-6,9,11-trihydroxy-5,12(8H)-naphthacenedione 9-acetate.

In accordance with all of the foregoing procedures but where in place of mercuric acetate, there is utilized mercuric trifluoroacetate, mercuric propionate, mercuric valerate, or mercuric benzoate, there are obtained the corresponding 9-acetyl trifluoroacetate, propionates, valerates, or benzoates, respectively.

EXAMPLE XI 7,10-Dihydro-6,9,11-trihydroxy-5,12(8H)-naphthacenedione, also known as 4-Demethoxy (+)-7-deoxydaunomycinone (IX b)

9-Acetyl-7,10-dihydro-6,9,11-trihydroxy-5,12-(8H)-naphthacenedione-9-acetate (100 mg) was dissolved in ethanol (30 ml) and water (17.5 ml). The solution was degassed and flushed with nitrogen 3 times. To the resulting mixture was added 0.5N aqueous sodium hydroxide (5 ml) and the resultant solution degassed and flushed with nitrogen. The mixture was stirred at room temperature for 30 minutes. The reaction mixture was diluted with water and extracted with chloroform. The extract was dried over anhydrous sodium sulfate. The solvent stripped off under reduced pressure to yield red solid residue 7,10-dihydro-6,9,11-trihydroxy-5,12(8H)-naphthadenedione, also designated as 4-demethoxy-(+);-7-deoxydaunomycinone (90 mg, 100% yield). m.p. 160°–162° C ($CH_3CO_2H$); UV ($CHCl_3$) 290, 460, 484, 518 nm; IR 5.90, 6.20, 6.35$\mu$; PFT ($CDCl_3$) $\delta$13.48 (s 2H OH's), 8.35 (m 2H aryl), 7.82 (m 2H aryl), 3.01 (m 4H benzylic), 2.39 (s 3H $OCCH_3$), 1.99 (m 2H benzylic), 1.60 (s 1H OH), (exchangeable with $D_2O$).

In accordance with the above procedure but starting with (+)-7-deoxy-1-methoxy daunomycinone 9-acetate there is obtained (+)-7-deoxy-1-methoxydaunomycinone. NMR (partial): $\delta$= 2.39 (s, 3H), 4.04 (s, 6H), 7.44 (s, 2H), 13.81 (s, 1H), 13.83 (s, 1H); MS: m/e 412, 394, 379, 369, 351.

In accordance with the above procedure but starting with (+)-4-demethoxy-1,4-dimethyl or 2,3-dimethyl-7-deoxydaunomyc-none 9-acetate, there is obtained the corresponding (+)-4-demethoxy-1,4-dimethyl or 2,3-dimethyl-7-deoxydaunomycinone.

In accordance with the foregoing procedures, but starting instead with any of the other 9-acetyl9-esters produced in accordance with Example X, there is produced the corresponding 9-acetyl carbinol.

EXAMPLE XII

4-Demethoxydaunomycinone (XI) and 4-demethoxy-7-epi-daunomucinone (X)

a. Dry nitrogen was bubbled rapidly through a solution of (+)-4-demethoxy-7-deoxydaunomycinone (23 mg) in carbon tetrachloride (50 ml). The solution was irradiated with a GE-sunlamp while a solution of bromine in carbon tetrachloride (3 equiv. excess) was added very slowly with stirring. The reaction is periodically monitored using h.p.l. c. (three 2 foot ×⅛inch Corasil columns eluted with chloroform in a Waters h.p.l.c. unit, flow rate 0.6ml/min.). Bromine addition and irradiation are continued for 30 minutes until h.p.l. c. shows disappearance of over 80% of the starting material. The solution is concentrated and the residue was taken up in dimethyl sulfoxide (2 ml), silvertrifluoroacetate (20 mg) was was added, the reaction stirred for 10 minutes, quenched in water and after 10 further minutes extracted with chloroform which was dried over sodium sulfate and stripped off to yield a residue.

b. An 0.25 mm silica gel G.F. tlc plate (Analtech) was pretreated by elution with 3% methanol in methylene chloride and allowed to air dry in a hood. The residue from solution (a) was then carefully applied and the plate eluted as usual with 3% methanol in methylene chloride. Bands corresponding to (+)-4-demethoxydaunomycinone ($R_f$ = 0.25), (+)-4-demethoxy-7-epidaunomycinone ($R_f$ = 0.19) and a little starting material ($R_f$ = 0.53) were separately isolated, extracted with 10% methanol in methylene chloride and concentrated. The above $R_f$ values refer to hydrated plates using daunomycinone ($R_f$ 0.27) as a reference. Each residue was taken up in chloroform and filtered through a glass fiber plug and concentrated.

From this procedure there are obtained the following products: 4-demethoxy-7-epidaunomycinone (9 mg), 4-demethoxydaunomycinone (7 mg), and starting material (1 mg).

4-demethoxydaunomycinone: MS: 368, 350, 348, 332, 317, 307, 289, 279, 261, 233; NMR: $\delta$2.31 (m, 2H), 2.44 (s, 3H), 3.08 (m, 2H), 4.56 (s, 1H OH), 5.32 (m, 1H, $\nu\frac{1}{2}$ = 8 Hz), 7.84 (m, 2H), 8.31 (m, 2H), 13.29 (s, 1H), 13.48 (s, 1H), 4-demethoxy-7-epidaunomycinone: NMR: $\delta$2.28 (m, 2H), 2.41 (s, 3H), 3.03 (m, 2H), 3.89 (s, 1H), 4.26 (s, 1H), 5.40 (m, 1H, $\nu\frac{1}{2}$ = 18 Hz), 7.84 (m, 2H), 8.31 (m, 2H), 13.31 (s, 1H), 13.94 (s, 1H).

In accordance with the above procedures but starting with (+)-1-methoxy-7-deoxy-daunomycinone there is obtained starting material, (+)-methoxydaunomycinone and (+)-7-epi-1-methoxydaunomycinone having $R_f$ values of 0.25, 0.22 and 0.17 respectively

EXAMPLE XIII

Epimerization of (+)-4-demethoxy-7-epidaunomycinone (X) to (+)-4-demethoxydaunomycinone (XI)

The (+)-4-demothoxy-7-epidaunomycinone (2.4 mg) above was taken up in trifluoroacetic acid (1.5 ml) and the solution allowed to stand 2 hours at room temperature. The reaction was poured into water (5 ml), extracted with chloroform and the chloroform washed well with water, then dried over sodium sulfate. Chromatography as described above (3% methanol/methylene chloride) gave (+)-4-demethoxydaunomycinone as the major product (1.8 mg) accompanied by traces of (+)-4-demethoxy-7-epidaunymycinone, a non-polar purple band, and 2 less polar orange bands.

In accordance with the above procedure but starting with (+)-1-methoxy-7-epidaunomycinone, (+)-4-demethoxy-1,4-dimethyl-7-epidaunomycinone and (+)-4-demethoxy-2,3-dimethyl-7-epidaunomycinone, there is obtained the corresponding (+)-1-methoxydaunomycinone (+)-4-demethoxy-1,4-dimethyl-daunomycinone and (+)-4-demethoxy-2,3-dimethyl-daunomycinone.

EXAMPLE XIV

Resolution of (+)-4-demethoxydaunomycinone (XI)

Racemic (+)-4-demethooxydaunomycinone (10 mg) is taken up in dry benzene (2 ml) and dry pyridine (3 drops) are added, followed by freshly prepared l-methoxyacetyl chloride (30 mg). The reaction mixture is refluxed for 30 minutes, allowed to cool, then poured into water and extracted with chloroform. The chloroform extracts are combined, washed with 5% aqueous oxalic acid, followed by water and brine. The chloroform are dried over anhydrous sodium sulfate, concentrated at reduced pressure, and the residue applied to a preparative thin-layer plate of silica gel. Elution with 3% methanol in methylene chloride (v/v) produces an orange band corresponding to the l-methoxyacetyl ester which is carefully removed and extracted with 10% methanol in methylene chloride, then the eluate concentrated and rechromatographed in the identical manner. There is thus obtained the 1-methoxyacetyl ester (at C-7 OH) of (+)-daunomycinone.

The 1-menthoxyacetyl ester is dissolved in ethanol (2 ml), the solution degassed and flushed with nitrogen three times, and several drops of 2M sodium hydroxide are added. The resulting solution is again degassed and flushed with nitrogen, then stirred at 25° for 3 hours. The mixture is poured onto ice and dilute aqueous oxalic acid, extracted with chloroform, the extracts washed and dried over anhydrous sodium sulfate. After solvent removal, the residue is chromatographed on silica and the (+)-4-demethoxydaunomycinone isolated.

In accordance with the above procedure but starting with (+)-1-methoxydaunomycinone, (+)-4-demethoxy-1,4-dimethyldaunomycinone and (+)-4-demethoxy-2,3-dimethyldaunomycinone, there is obtained the corresponding (+)-1-methoxydaunomycinone (+)-4-demethoxy-1,4-dimethyldaunomycinone and (+)-4-demethoxy2,3-dimethyldaunomycinone.

We claim:
1. Ethers having the formula

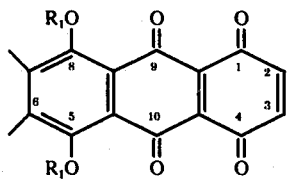

wherein $R_1$ is a lower alkyl of 1–5 carbon atoms; phenyl- or substituted phenyl-lower alkyl wherein the substituent groups are lower alkyl, lower alkoxy, each containing 1–5 carbon atoms, or halo; and lower alkyl contains 1–5 carbon atoms.

2. Ethers of claim 1 wherein $R_1$ is lower alkyl of 1–5 carbon atoms or phenyl-lower alkyl containing 1–5 carbon atoms in the alkyl moiety.

3. Ethers of claim 1 wherein $R_1$ is methyl or benzyl.

4. Process for the preparation of a compound of claim 1 which comprises oxidizing a derivative of 1,4,5,8-hydroxy anthraquinnone of the formula

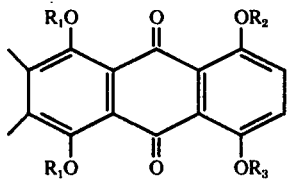

wherein $R_1$ has the same definition as in claim 1 $R_2$ and $R_3$ are hydrogen, lower alkyl, phenyl-lower alkyl, substituted phenyl-lower alkyl wherein the substituents are lower alkyl, lower alkoxy or halo, wherein the moiety lower alk contains 1–5 carbon atoms and $R_1$, $R_2$ and $R_3$ may be the same or different.

5. A process of claim 4 wherein $R_1 = R_2 = R_3$.

6. A process of claim 5 wherein $R_1 = R_2 = R_3 =$ lower alkyl.

7. A process of claim 4 wherein $R_1 = R_2 = R_3 =$ methyl and the oxidizing agent is argentic oxide in the presence of an acid.

8. A process of claim 4 wherein the oxidizing agent is argentic oxide in the presence of nitric acid.

9. A compound of the formula

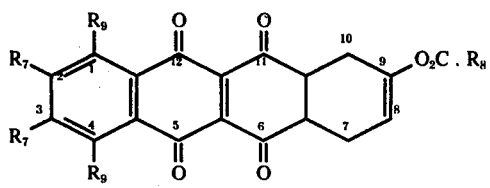

wherein $R_7$ is lower alkyl of 1–5 carbon atoms or hydrogen, $R_9$ is $R_1$, $R_1O$, or hydrogen, where when $R_7$ is lower alkyl $R_9$ is hydrogen and when $R_9$ is $R_1$ or $R_1O$, $R_7$ is hydrogen, $R_8$ is selected from a group consisting of the same moieties as $R_1$, wherein $R_1$ is as defined in claim 1.

10. A compound of claim 9 wherein $R_8 =$ lower alkyl.

11. A compound of claim 9 where $R_7$ is methyl or hydrogen $R_8$ is methyl, phenyl or hydrogen and $R_9$ is methyl, methoxy, or hydrogen.

12. The process of preparing a compound of claim 9 which comprises subjecting a compound of the formula

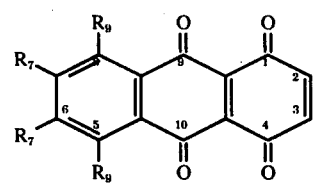

to a Diels-Alder condensation with a compound of the formula

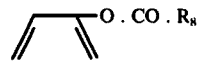

wherein $R_7$, $R_8$ and $R_9$ are as defined in claim 9.

13. A compound of the formula

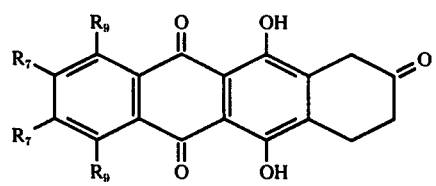

wherein $R_7$ and $R_9$ are as defined in claim 9.

14. A compound of claim 13 wherein $R_7$ is methyl or hydrogen and $R_9$ is methyl, methoxy or hydrogen.

15. A compound having the formula

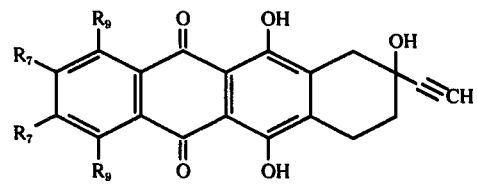

wherein $R_1$, $R_7$ and $R_9$ are as defined in claim 9.

16. A compound of claim 15 wherein $R_7$ is lower alkyl or hydrogen and $R_9$ is lower alkoxy or hydrogen.

17. A compound of claim 16 wherein $R_7$ is methyl or hydrogen and $R_9$ is methyl, methoxy or hydrogen.

18. A process of preparing a compound of claim 15 which comprises reacting a compound of the formula

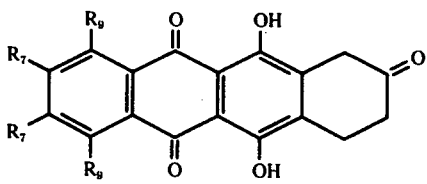

wherein $R_7$ and $R_9$ are as defined in claim 15 with an ethynylating agent.

19. A process of claim 18 wherein the ethynylating agent is M.C ≡ CH or CH ≡ C.MgX where M is an alkali or alkaline earth metal and X is Cl, Br or I.

20. A process of claim 19 wherein $R_7$ is methyl or hydrogen, $R_9$ is methoxy or hydrogen and the ethynylating agent is CH ≡ C.MgBr.

21. A process of preparing a compound of the formula

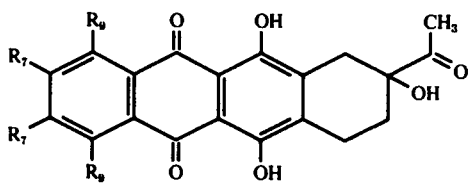

wherein $R_7$ and $R_9$ are defined in claim 15 which comprises reacting a compound of claim 15 with hydrating agent. comprises reacting a compound of claim 15 with hydrating agent.

22. A process of claim 21 wherein the hydrating agent is mercuric ion.

23. A process of claim 21 where $R_1$ is other than hydrogen, the hydrating agent is a sequence of a mercuric lower alkanoate in the presence of a lower alkyl alkanoate, hydrogen sulphide, aqueous alkali metal hydroxide in a lower alkanol and aqueous mineral acid, wherein lower alkyl, lower alkanoate and lower alkanol each contain 1-5 carbon atoms.

24. A process of claim 21 where $R_1$ is hydrogen, the hydrating agent is a sequence of a mercuric lower alkanoate in the presence of a lower alkyl alkanoate, and hydrogen sulphide, wherein lower alkyl and lower alkanoate each contain 1-5 carbon atoms.

25. A compound of the formula

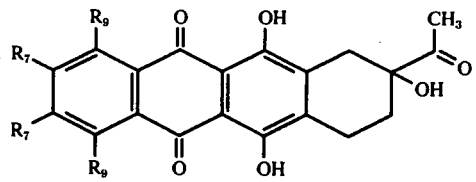

wherein $R_7$ and $R_9$ are as defined in claim 9.

26. A compound of claim 25 where $R_7 = R_9 =$ hydrogen.

27. A compound of claim 25 where $R_7 =$ lower alkyl, $R_9 =$ hydrogen.

28. A compound of claim 27 where $R_7 =$ methyl.

29. A compound of claim 25 where $R_7 =$ hydrogen and $R_9 =$ lower alkoxy.

30. A compound of claim 25 where $R_9 =$ methoxy.

31. A compound of claim 25 where $R_7$ is hydrogen and $R_9$ is lower alkyl.

32. A compound of claim 25 where $R_9$ is methyl.

33. The process which comprises reacting a compound of claim 25 with a free radical source of bromine in the presence of means for reducing the concentration of the hydrobromic acid produced in the course of the reaction, and replacing the bromine thus introduced with hydroxyl by hydrolyzing with a hydrolyzing agent to yield a mixture of the formula

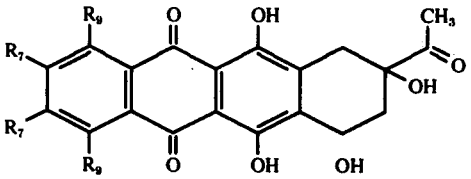

wherein $R_7$ and $R_9$ are as defined in claim 25.

34. A process of claim 33 wherein the hydrolyzing agent is selected from the group consisting of water, mild base, alumina, and silica gel.

35. A process of claim 33 wherein the hydrolyzing agent comprises the sequential treatment of an ester or silver salt of an alkanoic or halo alkanoic acid and a base.

* * * * *

UNITED STATES PATENT AND TRADEMARK OFFICE
CERTIFICATE OF CORRECTION

PATENT NO. : 4,021,457

DATED : May 3, 1977

INVENTOR(S) : Andrew S. Kende, John E. Mills, Yuh-Geng Tsay

It is certified that error appears in the above-identified patent and that said Letters Patent are hereby corrected as shown below:

COLUMNS 1 and 2,

Amend the structural formulae IX (a,b) through XI to read as follows:

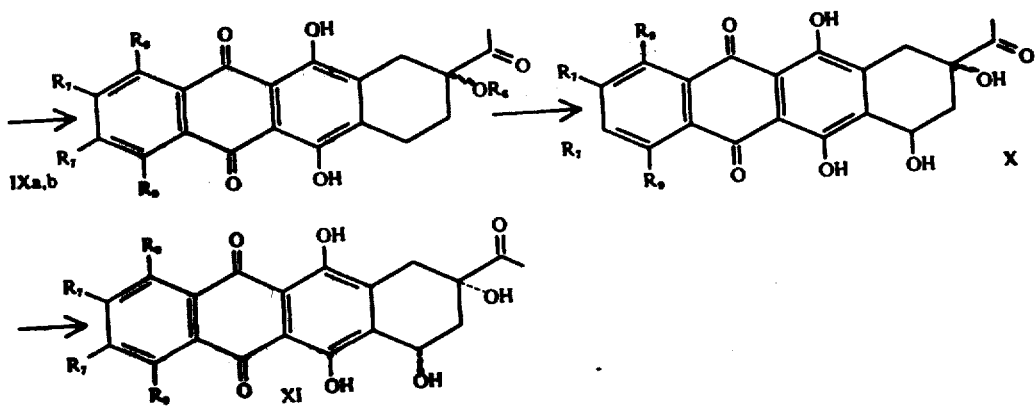

UNITED STATES PATENT AND TRADEMARK OFFICE
CERTIFICATE OF CORRECTION

PATENT NO. : 4,021,457
DATED : May 3, 1977
INVENTOR(S) : Andrew S. Kende, John E. Mills, Yuh-Geng Tsay It is certified that error appears in the above-identified patent and that said Letters Patent are hereby corrected as shown below:

Amend the formula in Claim 33 to read as follows:

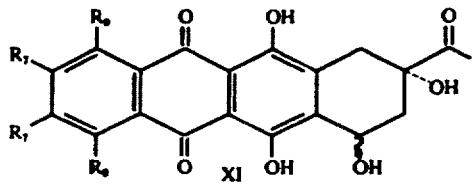

Signed and Sealed this

Tenth Day of July 1979

[SEAL]

Attest:

*Attesting Officer*

LUTRELLE F. PARKER
*Acting Commissioner of Patents and Trademarks*